US008926951B2

(12) United States Patent
Ratcliff et al.

(10) Patent No.: US 8,926,951 B2
(45) Date of Patent: Jan. 6, 2015

(54) COMPOSITION FOR PREVENTING ORAL DISEASE BY PENETRATING POLYMICROBIAL ORAL BIOFILMS AND KILLING ORAL PATHOGENS

(75) Inventors: James L. Ratcliff, Pueblo West, CO (US); David R. Drake, Iowa City, IA (US); Sally A. Cunningham, Monroe, WA (US); Elena J. Young, Scottsdale, AZ (US)

(73) Assignee: Micropure, Inc., Scottsdale, AZ (US)

( * ) Notice: Subject to any disclaimer, the term of this patent is extended or adjusted under 35 U.S.C. 154(b) by 747 days.

(21) Appl. No.: 12/731,271

(22) Filed: Mar. 25, 2010

(65) Prior Publication Data

US 2010/0221198 A1 Sep. 2, 2010

Related U.S. Application Data

(63) Continuation-in-part of application No. 11/774,730, filed on Jul. 9, 2007.

(60) Provisional application No. 61/211,097, filed on Mar. 26, 2009.

(51) Int. Cl.
*A61K 8/19* (2006.01)
*A61Q 11/00* (2006.01)
*A61K 33/40* (2006.01)
*A61K 9/00* (2006.01)
*A61K 8/20* (2006.01)
*A61K 8/22* (2006.01)

(52) U.S. Cl.
CPC ............... *A61K 33/40* (2013.01); *A61K 9/0063* (2013.01); *A61K 8/20* (2013.01); *A61K 8/22* (2013.01); *A61Q 11/00* (2013.01)
USPC ................................. 424/53; 424/49; 424/401

(58) Field of Classification Search
USPC .................................................. 424/49, 422
See application file for complete search history.

(56) References Cited

U.S. PATENT DOCUMENTS

| 3,271,242 | A | 9/1966 | McNicholas et al. |
| 4,084,747 | A | 4/1978 | Alliger |
| 4,330,531 | A | 5/1982 | Alliger |
| 4,689,215 | A | 8/1987 | Ratcliff |
| 4,696,811 | A | 9/1987 | Ratcliff |
| 4,786,492 | A | 11/1988 | Ratcliff |
| 4,788,053 | A | 11/1988 | Ratcliff |
| 4,792,442 | A | 12/1988 | Ratcliff |
| 4,793,989 | A | 12/1988 | Ratcliff |
| 4,808,389 | A | 2/1989 | Ratcliff |
| 4,818,519 | A | 4/1989 | Ratcliff |
| 4,837,009 | A | 6/1989 | Ractliff |
| 4,851,213 | A | 7/1989 | Ratcliff |
| 4,855,135 | A | 8/1989 | Ratcliff |
| 4,886,657 | A | 12/1989 | Ratcliff |
| 4,889,714 | A | 12/1989 | Ratcliff |
| 4,925,656 | A | 5/1990 | Ratcliff |
| 4,975,285 | A | 12/1990 | Ratcliff |
| 5,200,171 | A | 4/1993 | Ratcliff |
| 5,348,734 | A | 9/1994 | Ratcliff |
| 5,489,435 | A | 2/1996 | Ratcliff |
| 5,618,550 | A | 4/1997 | Ratcliff |
| 5,738,840 | A | 4/1998 | Richter |
| 6,231,830 | B1 | 5/2001 | Madray |
| 6,350,438 | B1 | 2/2002 | Witt et al. |
| 6,696,047 | B2 | 2/2004 | Scott et al. |
| 2009/0016973 | A1 | 1/2009 | Ratcliff et al. |
| 2010/0015207 | A1 | 1/2010 | Speronello et al. |

FOREIGN PATENT DOCUMENTS

EP 0613678 9/1994

OTHER PUBLICATIONS

Villhauer A, Olson B, Drake D. Bactericidal Activity of Stabilized Chlorine Dioxide Against Polymicrobial Biofilms. 2009 International Association for Dental Research Poster #3417, General Session, Apr. 1-4, 2009.
Villhauer A, Horst J, Olson B and Drake D. Bactericidal Activity of Stabilized chlorine dioxide rinse. American Association for Dental Research Meeting and Exhibition Abstract 0946, Apr. 4, 2008.
Drake, David. Final Report: Phase III Biofilm Studies. Feb. 13, 2008. Rowpar Pharmaceuticals, Inc.
Benarde MA, Snow WB, Olivieri VP, Davidson B., Kinetics and Mechanism of Bacterial Disinfection by Chlorine Dioxide, J. Applied Microbiology, 1967, vol. 15, p. 257-265.
Berg JD, Roberts PV, Matin A., Effect of Chlorine Dioxide on Selected Membrane Functions of *Escherichia Coli*, Journal of Applied Bacteriology, 1986, vol. 60, pp. 213-220.
Lynch E., Sheerin A., et al., Multicomponent Spectroscopic Investigations of Salivary Antioxidant Consumption by an Oral Rinse Preparation Containing the Stable Free Radical Species Chlorine Dioxide (ClO2), Free Rad. Res, 1997, vol. 26, pp. 209-234.
Masschelein WJ, Chlorine Dioxide: Chemistry and Environmental Impact of Oxychlorine Compounds, 1979 Ann Arbor Science Publishers Inc., pp. 153-156.
Roller SD, Olivieri VP, Kawata K., Mode of Bacterial Inactivation by Chlorine Dioxide, Water Research 1980, vol. 14, pp. 635-641.
Silwood CJL, Grootveld MC, Lynch E., A Multifactorial Investigation of the Ability of Oral Health Care Products (OHCPs) to Alleviate Oral Malodour, Journal of Clinical Periodontol, 2001, vol. 28, pp. 634-641.

(Continued)

*Primary Examiner* — Walter Webb
(74) *Attorney, Agent, or Firm* — The von Hellens Law Firm, Ltd.

(57) ABSTRACT

A composition and method of stabilized chlorine dioxide at a concentration range of about 0.005% to about 0.800% (w/v) at a pH in the range of 6.0 to 7.4 for the prevention of oral diseases caused by dental biofilm and plaque accumulation, such as gingivitis and periodontitis, through bactericidal properties is disclosed. The bactericidal properties of stabilized chlorine dioxide are further expanded to include reduction (kill) of anaerobic/aerobic/facultative gram-negative and gram-positive oral bacteria occurring in plaque or polymicrobial biofilms. The composition may be in the form of wash, rinse, soak, paste, gel, aerosol spray, or other suitable delivery system.

11 Claims, 3 Drawing Sheets

(56) References Cited

OTHER PUBLICATIONS

Wirthlin MR, Marshall GW Jr., Rowland RW, Formation and Decontamination of Biofilms in Dental Unit Waterlines, Journal of Periodontology, 2003, vol. 74(11), pp. 1595-1609.

Benarde MA, Snow WB, Olivieri VP, Davidson B. Kinetics and Mechanism of Bacterial Disinfection by Chlorine Dioxide. J Appl Microbiology. 1967; 15:257-65.

Berg JD, Roberts PV, and Matin A. Effect of chlorine dioxide on selected membrane functions of *Escherichia coli*. Journal of Applied Bacteriology. 1986; 60:213-220.

Hojo K, Nagaoka S, Ohshima T, and Maeda N. Bacterial Interaction in Dental Biofinn Development. Journal of Dental Research. 2009; 88(11): 982-990.

Lynch E, Sheerin A, Claxon AWD, et al. Multicomponent Spectroscopic Investigations of Salivary Antioxidant Consumption by an Oral Rinse Preparation Containing the Stable Free Radical Species Chlorine Dioxide (ClO2). Free Rad. Res. 1997; 26: 209-234.

Masschelein, WJ. Chlorine Dioxide: Chlorine and Environmental Impact of Oxychlorine Compounds. (1979) Ann Arbor: Ann Arbor Science Publishers, Inc.

Roller SD, Olivieri VP, Kawata K. Mode of Bacterial Inactivation by Chlorine Dioxide. Water Research 1980; 14:635-41.

Silwood CJL, Grootveld MC, Lynch E. A multifactorial investigation of the ability of oral health care products (OHCPs) to alleviate oral malodour. J Clin Periodontol. 2001; 28: 634-641.

Wirthlin MR, Marshall GW Jr, Rowland RW. Formation and Decontamination of Biofilms in Dental Unit Waterlines. Journal of Periodontology 2003; 74(11):1595-1609.

AAS,J.A., Paster, B.J., Stokes, L.N., et al., Defining the Normal Bacterial Flora of the Oral Cavity. Journal of Clinical Microbiology, Nov. 2005; vol. 43, p. 5721-5732.

Levitt, B.A. and Gregory, R.L., Antibiotics and Dental Biofilms. The Journal of Professional Excellence: Dimensions of Dental Hygiene, Jan. 2012; 10(1); p. 56-59.

Shemesh, M., Kolter,R. and Losick, R., The Biocide Chlorine Dioxide Stimulates Biofilm Formation in *Bacillus subtilis* by Activation of the Histidine Kinase KinC, Journal of Bacteriology, Dec. 2010; vol. 192(24); p. 6352-6356.

Grootveld, M.C., Silwood, C.L., Lynch, E. et al., Abstract: H NMR-Linked Chemometric Analysis of Control and Dentifrice-Treated Human Saliva, IADR/AADR/CADR 87th General Session and Exhibition. Apr. 2009.

Silwood, C.L., Grootveld, M.C. and Lynch, E., A multifactorial investigation of the ability of oral health care products (OHCPs) to alleviate oral malodour. J Clin Periodontol. 2001; 28: p. 634-641.

US 8,926,951 B2

COMPOSITION FOR PREVENTING ORAL DISEASE BY PENETRATING POLYMICROBIAL ORAL BIOFILMS AND KILLING ORAL PATHOGENS

CROSS REFERENCE TO RELATED APPLICATIONS

The present application is a continuation-in-part of an application entitled "Composition and Method for the Prevention of Oral Disease" filed Jul. 9, 2007 and assigned Ser. No. 11/774,730 and claims priority to the disclosure contained in a provisional patent application entitled "Composition and Method for the Prevention of Oral Disease", filed Mar. 26, 2009 and assigned Ser. No. 61/211,097, both of which are assigned to the present assignee.

BACKGROUND OF THE INVENTION

1. Field of the Invention

The present invention relates to the composition in the form of wash, rinse, soak, paste, gel, aerosol spray, or other suitable delivery system and method for the prevention of oral diseases with the use of stabilized chlorine dioxide and establishing the bactericidal properties at a concentration range of about 0.005 to about 0.800% (w/v) to significantly reduce bacterial accumulation and to act as an antimicrobial on both gram-negative anaerobic/aerobic/facultative and gram-positive anaerobic/aerobic/facultative oral bacteria in plaque and polymicrobial dental biofilm environments.

2. Description of Related Art

Dental plaque is a diverse community of microorganisms found on the tooth surface embedded in an extracellular matrix of host and microbial polymers. Dental plaque can occur above (supragingival) and below (subgingival) the gumline. Plaques that form on subgingival tooth surfaces and coat the epithelium lining of the gingival crevice lead to the development of periodontal infections (i.e., gingivitis and periodontitis).

Supragingival dental plaque forms on teeth within hours after they are cleaned. In the presence of a diet rich in sucrose, shifts occur in the supragingival plaque to more of an acidogenic plaque, with dental caries as an outcome. Salivary proteins such as mucins, proline-rich proteins, staherins, histatins, and cystatins have a strong affinity for the hydroxyapatite mineral of teeth. These proteins quickly bind to hydroxyapatite of the tooth to form a thick coating called the acquired pellicle. Certain bacteria in the oral cavity selectively adhere to the pellicle, begin to divide, and form microbial communities. Initially, approximately 80% of the bacteria that colonize pellicle-coated tooth surfaces are facultative, gram-positive, non-motile cocci, such as *Streptococcus* (sanguis) *sanguinis* (U.S. Pat. No. 4,889,714). The other 20% include a variety of gram-negative bacteria such as *Veillonella* species. As the microbial communities grow, the environment changes due to the metabolic activities of these early colonizers and the addition of diverse groups of other bacteria to the plaque mass. An important environmental change in the plaque is the development of a low-oxygen environment that promotes the colonization and growth of anaerobic bacteria. Microorganisms in the plaque synthesize a slime matrix or glycocalyx from abundant polysaccharides, glycoproteins, and dietary sugars (e.g., sucrose) present in the oral environment. Eventually, the plaque becomes a characteristic dental biofilm with a highly structured, matrix-embedded, diverse microbial population altering gene expression severely.

Bacteria in dental biofilm are the major cause of several oral diseases including gingivitis, chronic and aggressive periodontitis, and necrotizing periodontal diseases. Gingivitis is the gingival inflammation without loss of connective tissues around teeth caused by undisturbed dental biofilm. Studies have shown that gingivitis will develop within 10-21 days without oral hygiene practices allowing for the accumulation of plaque. Approximately 80% of U.S. adults have a case of gum/periodontal disease. Gingivitis is preventable by routine oral care, but if untreated may lead to a severe gum disease known as periodontitis. Periodontitis is characterized by a group of infections which destroy supporting tissue and bone by plaque-induced inflammation. Chronic periodontitis is the most common form affecting approximately 20% of the adult U.S. population. Symptoms include the formation of deep periodontal pockets, gingival recession, increased tooth mobility, and loss of bone as detected by radiographs. If left untreated, periodontitis can lead to tooth loss.

A review of bacterial interactions in dental biofilm completed by Hojo, et al. (2009) shows the diversity of bacterial communities in dental biofilms. First colonizers, including *Streptococcus sanguinis*, adhere to teeth allowing for other planktonic bacteria, which are unable to adhere to teeth, to attach to it and begin colonizing, eventually developing into a biofilm. The bacterial co-aggregation on the tooth surface causes the behavioral change including increased resistance toward topical antimicrobial agents and decreasing efficacy. Hojo et al. describes further that the complexity physically restricts the antimicrobial agents due to less sensitivity developed by the polymicrobial biofilm.

Supporting evidence confirms that the present invention acts as an antimicrobial against both gram-negative anaerobic/aerobic/facultative and gram-positive anaerobic/aerobic/facultative oral bacteria in polymicrobial dental biofilm environments.

The term chlorine dioxide is widely used in the industry. Those skilled in the art will and do appreciate the various forms or variations thereof, which are available to perform certain intended functions and purposes. Furthermore, U.S. Pat. No. 3,271,242 describes a form of stabilized chlorine dioxide and a method of making the product, which is particularly useful in carrying out the present invention.

The use of chlorine dioxide for sanitation was first suggested in 1948 by Eric Woodward to reduce the incidence of unpleasant taste in shrimp. Since then, chlorine dioxide [$ClO_2$] use has spread into a number of other industries. The oxidative power of $ClO_2$ is used in the manufacturing of wood pulp as an agent for the bleaching of cellulose fibers. In water treatment, $ClO_2$ has become widely used for water sanitation. In this case, it has been shown to be effective at reducing the bacterial content, algae content, and odor associated with wastewater treatment. Additionally, the utilization of $ClO_2$ for treating drinking water has been effective without adversely affecting its taste. The benefits of $ClO_2$ over other processes utilizing ozone or bleach for example, are reduced cost, reduced toxicity and reduced production of chlorinated by-products.

In 1999 the EPA published "Alternative Disinfectants and Oxidants Guidance Manual," describing disinfectant uses for $ClO_2$ and containing information on the mechanism of generation, application and standards and regulations governing use of $ClO_2$ and other disinfectants. Major applications listed by table 4-5, section 4.8.2 in the manual are as follows: primary or secondary disinfectant, taste control, odor control, TTHM/HAA reduction (total trihalomethanes are chlorinated organics, chloroform [$CHCl_3$] and dichlorobromomethane [$CHCl_2Br$] for example; haloacetic acids are created when an atom from the halogen group, chlorine, for example, replaces a hydrogen on the acetic acid molecule), Fe and Mn control, color removal, sulfide destruction, phenol destruction and Zebra mussel control [EPA 1999, p. 4-34]. These are accomplished by oxidation of various substances found in water. For example, unpleasant tastes and odors (sulfides, phenols, others) can exist in water due to vegetative decay and algae content. $ClO_2$ reduces these tastes either by eliminating the source (algae) or oxidizing the causative taste and odor molecules. In the control of iron and manganese, $ClO_2$ will bring the dissolved ions out of solution to form precipitates, which may be eliminated through filtration and/or sedimentation. Zebra mussel control is important because it helps to maintain the natural ecology of a body of water. Zebra mussels are organisms that will infest a lake or river, strip it of nutrients and create a pseudo-fecal mucous layer on the bottom. The use of $ClO_2$ for water sanitation and pulp treatment generally involves on-site generation followed by immediate use.

The term 'stabilized chlorine dioxide' on the other hand, refers to the generation and subsequent sequestration of $ClO_2$, which allows for its storage and availability for later use. The first reference to stabilized chlorine dioxide in a patent was in U.S. Pat. No. 2,482,891 in which $ClO_2$ is stabilized in a powder for storage. For its application, it is mixed with water to "liberate" the chlorine dioxide. A method and composition for the use of aqueous stabilized chlorine dioxide for antiseptic purposes was noted in U.S. Pat. No. 3,271,242. The 1979 text Chlorine Dioxide, Chemistry and Environmental Impact of Oxychlorine Compounds, describes (aqueous) stabilized chlorine dioxide as follows:

"The stabilization of chlorine dioxide in aqueous solution was proposed by using perborates and percarbonates. Thus, a stabilized solution of $ClO_2$ would be obtained at pH 6 to 8 by passing gaseous $ClO_2$ into an aqueous solution containing 12% $Na_2CO_3.3H_2O_2$. Other variants are possible. In reality, it seems that in these methods, the chlorine dioxide is practically completely transformed to chlorite. Dioxide is released upon acidification." [Masschelein, 1979]

The reference to percarbonates and perborates may be replaced by the term 'peroxy compounds,' which would refer to any buffer suitable for maintaining the pH and hence, the stability of the $ClO_2$ in solution. The buffer is a necessary component, as the $ClO_2$ is unstable at low pH. Once the solution reaches low pH or encounters an area of low pH, the stabilized $ClO_2$ is released from solution and available for sanitation and oxidation.

In oral care products, the use of stabilized $ClO_2$ has been suggested as an active ingredient by a number of U.S. Pat. Nos. 4,689,215; 4,696,811; 4,786,492; 4,788,053; 4,792,442; 4,793,989; 4,808,389; 4,818,519; 4,837,009; 4,851,213; 4,855,135; 4,886,657; 4,889,714; 4,925,656; 4,975,285; 5,200,171; 5,348,734; 5,489,435; 5,618,550. Additionally, the use of stabilized $ClO_2$ has been suggested for the degradation of amino acids in U.S. Pat. No. 6,136,348. The premise for these products is that the stabilized chlorine dioxide will remain as such until it encounters the localized reductions in pH. Reduced pH levels can be a result of low pH saliva or oral mucosa, the accumulation of oral disease-causing bacteria or the presence of plaque biofilms on teeth and epithelial cells. Once released, the now active chlorine dioxide is effective at killing bacteria and oxidizing VSCs. Data have shown dramatic reduction in bacteria after exposures as short as 10 seconds, as set forth in U.S. Pat. No. 4,689,215. Additional data show remarkable decrease in VSCs in expired mouth air; the mechanism is believed to be oxidation of VSCs through the cleavage of the sulfide bonds.

The present invention relates to a composition containing stabilized chlorine dioxide that may be used for treatment of the mouth either in a solution, for example as a mouthwash, in concentrations below approximately 0.800% (w/v) for the control of disease-causing bacteria, bacterial plaque, and oral malodor. The rinse may be flavored with the addition of mint oils or extracts. The flavoring would not interact with stabilized chlorine dioxide or affect the stability of the formulation.

For liquids such as mouthwash, the standard unit of measurement when expressing concentration is weight-volume percentage. That is, a certain weight of component, solid, liquid, or dissolved in a solvent, is present in a certain volume of total mouthwash. Preferred concentrations of stabilized chlorine dioxide in this invention are in the range of 0.005% to 0.800% (w/v).

By "topical oral care composition" or "oral composition" as used herein is meant a product which is not intentionally swallowed for purposes of systemic administration of therapeutic agents, but is retained in the oral cavity for a sufficient time to contact substantially all of the dental surfaces and/or oral mucosal tissues for purposes of oral activity.

Previous inventions contemplate the use of stabilized chloride dioxide as a bactericide for the treatment gingivitis as well as a deodorizing agent for the treatment of oral malodor (Ratcliff, U.S. Pat. No. 4,689,215; Madray, U.S. Pat. No. 6,231,830; Richter, U.S. Pat. No. 5,738,840; Witt, U.S. Pat. No. 6,350,438). There is a large amount of evidence that indicates chlorine dioxide has bactericidal properties and that the chlorine dioxide serves to attack malodorous volatile sulfur compounds (VSC) in the mouth by splitting of the sulfide bonds (Lynch, 1997; Silwood, 2001).

Prior art compositions that have been used and tested have been accepted to an extent of efficacy in treating or preventing periodontitis, gingivitis, plaque accumulation and mouth odor. Prior Ratcliff patents have demonstrated the bactericidal effect of stabilized chlorine dioxide on *Streptococcus sanguinis* (U.S. Pat. Nos. 4,851,213 and 4,889,714). It is directed to a method of reducing dental plaque by altering the ecology of oral bacteria over a period of ten seconds by means of reducing the bacterium *S. sanguinis* by more than 90%. It also describes how the method breaks down double bonds in the glucosyltransferases present in the oral cavity.

Concentration range between 0.005-0.5% (w/v) chlorine dioxide with about 0.02%-3.0% phosphate is preferred in U.S. Pat. No. 5,348,734 by Ratcliff. This is the highest recited range in the prior art. The present invention is an extension with evidence that higher concentrations of stabilized chlorine dioxide are bactericidal for oral bacteria at a faster rate and in complex microbial environments, dental biofilm, than taught in the prior art.

Periodontal disease results from response to the polymicrobial ecology of subgingival plaque. The diverse and complex ecology of the oral cavity leads to a more resistant response to the immune system and antimicrobial drugs. In order to investigate a more natural environment of the oral cavity with periodontal disease, it is important to develop experimental conditions that mimic the diversity and complexity of the bacterial ecology. A limited number of studies that demonstrate considerable bacteria kill and inhibition of dental biofilm development on such microbial environments exist. The present invention takes into consideration the diverse natural ecology and investigates both the bactericidal properties in mixed microbial biofilms of several oral bacteria involved in periodontal diseases. Previous developments and prior research involve the investigation of single bacterial suspension cultures, which do not accurately represent the natural oral ecology on plaque development and dental biofilm.

The current invention is a continuation of related prior art research presented by Villhauer et al (2008). It contemplates the use of stabilized chlorine dioxide as a bactericidal and bacteriostatic agent against microorganisms involved in oral disease such as, but not limited to, *Porphyromonas gingivalis, Actinomyces odontolyticus* and *A. viscosus, Prevotella intermedia, Fusobacterium nucleatum, Micromonas micros, Streptococcus sanguinis* and *S. oralis, Campylobacter rectus*, and *Enterococcus faecalis*. The research shows bactericidal activity of the stabilized chlorine dioxide against a spectrum of oral bacteria, as single bacteria and as polymicrobial communities, associated with periodontal diseases and health. Polymicrobial biofilms of oral bacteria and the affect of stabilized chlorine dioxide solution as a bactericidal agent has also been examined.

U.S. Pat. No. 6,696,047 recites oral care compositions containing 0.02% to 6.0% of the chlorite ion at alkaline pH which are essentially free of chlorine dioxide (less than 2 ppm of chlorine dioxide)—and the novelty of these compositions are that the prescribed formulations are claimed to maintain stable amounts of the chlorite ion at 25° C. for one year or 40° C. for 3 months. According to the teachings in the patent, stability is exhibited in the composition if the following is observed at 25° C. for one year and/or 40° C. for three months: the chlorite ion is delivered in efficacious amounts to the oral cavity, the composition does not degrade to form chlorine dioxide, and the composition does not degrade excipients (with a change in flavor being a major indicator of degradation). A quantifiable percentage of acceptable chlorite ion degradation from time zero is not explicitly defined in the patent for any embodiment. The sample formulations that are presented to show stability of various embodiments (presented in the table labeled 'Results of Stability Testing') are all prepared at pH 10. Chlorite ion concentration, pH and flavor concentration are measured to demonstrate stability of the formulations. The compositions in U.S. Pat. No. 6,696,047 are designed for human and animal subjects, and while not specifically claimed in claims, the text of the patent indicates that these compositions may be used to treat and prevent diseases of the oral cavity, including caries. However, no claim is made that the composition without additional therapeutic agents has antimicrobial effects against polymicrobial dental biofilms in the oral cavity.

Biofilm growth is also a problem which occurs in dental unit water lines (DUWL). Some of the microbe genera detected in DUWL biofilms are *Actinomyces, Bacillus, Mycobacteria, Pseudomonas, Sphingomonas, Staphylococcus*, and *Streptococcus*. Stabilized chlorine dioxide solutions have been previously shown to be an effective decontaminant on biofilms that form in DUWLs. A specific study yielded results that indicated that stabilized chlorine dioxide outperformed alkaline peroxide in managing biofilm growth, by retaining a heterotrophic plate count (HPC) value of 0 after 5 days of treatment (Wirthlin et al., 2003).

There is no prior art that show evidence of antimicrobial properties of stabilized chlorine dioxide composition in the concentration range of about 0.005% to about 0.800% (w/v) on gram-negative anaerobic/aerobic/facultative and gram-positive anaerobic/aerobic/facultative oral bacteria in polymicrobial dental biofilm environments occurring in the oral cavity or with in vitro or in vivo experiments.

SUMMARY OF INVENTION

The present invention concerns oral care compositions including oral washes or rinses in a solution comprising stabilized chlorine dioxide. It contemplates the use of stabilized chlorine dioxide as a bactericidal agent against microorganisms found in polymicrobial dental biofilms involved in oral disease such as, but not limited to, *Porphyromonas gingivalis, Actinomyces viscosus, Fusobacterium nucleatum, Micromonas micros*, and *Streptococcus sanguinis*. The composition includes a range of 0.005%-0.800% (w/v) stabilized chlorine dioxide and may also take the form of an oral paste, gel, rinse, spray, powder, tray, varnish or similar, for the prevention of oral diseases significantly reducing bacterial accumulation and acting as an antimicrobial on both gram-negative anaerobic/aerobic/facultative and gram-positive anaerobic/aerobic/facultative oral bacteria in polymicrobial dental biofilm environments. The method includes the application of the composition in the oral cavity to produce an antimicrobial effect, sanitize, debride, and control the formation of bacterial plaque or dental biofilm and malodorous volatile sulfur compounds, the main contributors to oral diseases. The method may be applied daily or continuously as an antimicrobial/antiplaque/antibiofilm agent in the oral cavity.

The primary object of the present invention is to provide a composition, in a concentration in the range of about 0.005% to about 0.800% (w/v) stabilized chlorine dioxide for the prevention of oral diseases caused by dental biofilm, including gingivitis and periodontitis.

Another object of the present invention is to provide stabilized chlorine dioxide as an antimicrobial agent against oral microorganisms, gram-negative anaerobic/aerobic/facultative and gram-positive anaerobic/aerobic/facultative oral bacteria.

Yet another object of the present invention is to provide stabilized chlorine dioxide as an antimicrobial agent against oral microorganisms, gram-negative anaerobic/aerobic/facultative and gram-positive anaerobic/aerobic/facultative oral bacteria, in polymicrobial dental biofilms.

Still another object of the present invention is to provide a composition to produce antimicrobial effects following multiple exposures to eliminate oral microorganisms, gram-negative anaerobic/aerobic/facultative and gram-positive anaerobic/aerobic/facultative oral bacteria, in polymicrobial dental biofilms.

A further object of the present invention is to provide a composition to reduce but not eliminate oral organisms and bacteria associated with normal, healthy subgingival flora.

A yet further object of the present invention is to provide a method for applying the composition on a daily or continuous basis, as needed or as prescribed, to the oral cavity once or multiple times a day.

These and other objects and specific embodiments of the present invention will become apparent to those skilled in the art as the description thereof proceeds.

BRIEF DESCRIPTION OF THE DRAWINGS

The present invention will be described with greater specificity and clarity with reference of the following drawings, in which.

DETAILED DESCRIPTION OF THE INVENTION

Figure 1:
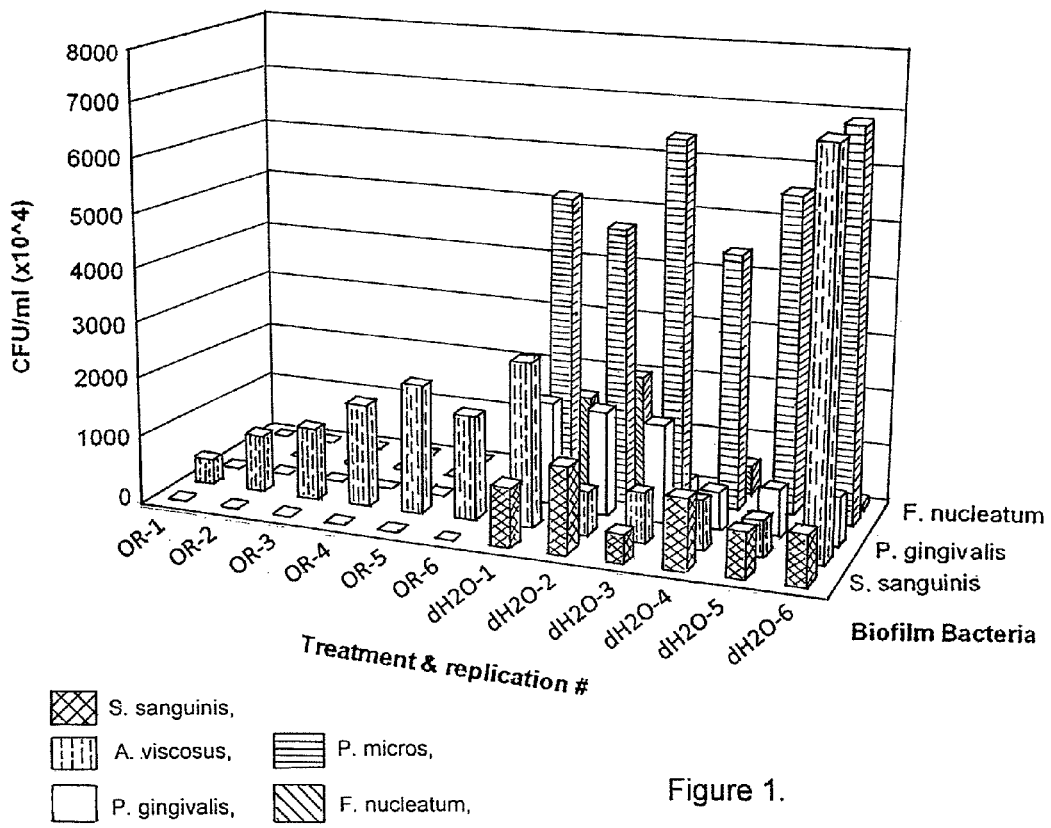
FIG. 1 illustrates a three dimensional bar chart of the test treatment versus control on polymicrobial biofilm.

The present invention is directed to oral care compositions including oral washes or rinses in a solution comprising stabilized chlorine dioxide, and may also take the form of a soak, paste, gel, aerosol spray, or other suitable delivery system. The effectiveness of the composition includes the determination of bactericidal activity of the stabilized chlorine dioxide against a spectrum of oral bacteria in a polymicrobial dental biofilm associated with periodontal diseases and health.

The present invention consists of a stabilized chlorine dioxide composition which acts as an antimicrobial on oral bacterial communities at a concentration range between 0.005%-0.800% (w/v). It has an effect of killing and reducing the number of gram-negative and gram-positive bacteria at concentrations higher than taught in the prior art.

The present invention teaches oral care compositions, including paste, gel, rinse, spray, powder, varnish or similar, in the form of a stabilized chlorine dioxide and a buffering system to achieve a specific pH of the final composition. The buffers may include acetate, citrate, phosphate buffers, and other buffers known to those skilled in the art. The oral care compositions include the following fundamental components:

a) 0.005% to 0.800% (w/w) or (w/v) of stabilized chlorine dioxide in the final composition; and b) A buffering system that achieves a pH of the final composition in a range of 6.0 to 7.4 and retards the escape of chlorine dioxide gas from the final composition The method taught herein delivers the composition to the human oral cavity (including but not limited to the teeth, tongue, gingiva, and saliva) through topical application of the composition to the human oral cavity, at least once daily.

The composition is not intended to be a dual phase composition and does not rely on the end user mixing ingredients immediately prior to use to produce chlorine dioxide, as described in the Alliger and Richter patents (U.S. Pat. Nos. 4,084,747, 4,330,531, 5,738,840).

Single-Phase Oral Rinse

A formulation for a single-phase oral rinse is disclosed below. The single phase oral rinse includes ingredients selected from the following components: Chlorine Dioxide, Citric Acid, Trisodium Phosphate, and Purified USP grade de-ionized water.

| Ingredient | Wt/Wt % |
|---|---|
| Chlorine Dioxide (Stabilized 5% solution) | 2.500% |
| Citric Acid | % to achieve a Final pH of 6.7-7.0 |

The remaining ingredients, e.g. trisodium phosphate and de-ionized water, are added in appropriate amounts to prevent the escape of chlorine dioxide and to balance the overall formulation, as is known to those skilled in the art. The final pH of the above oral rinse formulation is pH 6.7-7.0. Humectants, sweetening agents, and flavoring agents may be added to the above oral rinse embodiment in concentrations as is known to those skilled in the art.

Oral Rinse Preparation Procedure

Trisodium phosphate and aqueous soluble active ingredients (e.g. chlorine dioxide) are dissolved in de-ionized water. Citric acid is dissolved in de-ionized water in a separate preparation. Then, the citric acid preparation is added into and mixed with the aqueous preparation (containing chlorine dioxide) to achieve a pH of 6.7-7.0.

Use in the Oral Cavity

The composition is to be delivered to the oral cavity in the form of a wash, rinse, soak, paste, gel, aerosol spray, or other suitable delivery system. In the instance of a rinse, the consumer is instructed to swish with 15 mL of the rinse in the oral cavity for 30 seconds to 1 minute and expectorate the liquid once finished. The preferred frequency of administration would be two times a day (in the morning and at night before bed). This method applies to individuals older than 6 years of age.

The composition establishes the bactericidal kinetics of the antimicrobial characteristics of stabilized chlorine dioxide against mixed bacterial communities in dental biofilm at a concentration range of 0.005-0.800% (w/v). The experimental approach of evaluating bacteria as a biofilm and not as a single entity is important because oral bacteria do not occur in the mouth as single species, but as a community of complex and diverse bacterial species that eventually form dental biofilm and may cause oral disease absent disruption by oral hygiene. Conventional testing does not test bacterial kill in plaque-like environments or in polymicrobial suspensions, as was done in the present experiments. The oral cavity environment reduces the susceptibility to antimicrobials and makes it more difficult to control and prevent progression into diseased conditions.

The composition described herein acts as a bactericide on the following bacteria in biofilm: *Porphyromonas gingivalis*, *Fusobacterium nucleatum*, *Micromonas micros*, and *Streptococcus sanguinis*. It is believed to be effective on the majority of oral bacteria involved in the progression of oral diseases and periodontitis. When suspended in a polymicrobial biofilm environment of multiple species of oral bacteria, the present invention kills oral bacteria associated with oral diseases and opportunistic bacteria including those associated with health, more specifically both gram-negative anaerobic/aerobic/facultative and gram-positive anaerobic/aerobic/facultative oral bacteria. The invention also has less affect on oral bacteria associated with normal, healthy subgingival flora.

In summary, the present invention proclaims the use of stabilized chlorine dioxide oral rinse to be used as a bacteriostatic treatment on oral bacteria in dental biofilm environments. It also contemplates the ability of stabilized chlorine dioxide as an antimicrobial agent on oral bacteria involved in periodontal diseases with decreased affect on normal, healthy oral flora.

The specific mechanism of action of stabilized chlorine dioxide on oral organisms and biomolecules has not been fully investigated. It is believed that the present invention's bacteriostatic properties are due to inhibition of protein synthesis and/or to the inability of the cell to maintain membrane permeability and inhibited metabolic processes. Due to these effects on bacteria, dental biofilm production and progression to oral diseases can be inhibited by rinsing with a solution of the stabilized chlorine dioxide in a concentration range of 0.005% to 0.800% (w/v). The production of malodorous oral compounds (VSCs) are also reduced and inhibited.

It has been determined that the stabilized chlorine dioxide composition oxidatively consumes salivary biomolecules and creates products that may exert antimicrobial or bactericidal and bacteriostatic effects on the oral bacterial cells which ultimately gives rise to cell death. These effects can lead to control over the formation of bacterial biofilm and the adverse generation of malodorous VSCs, major contributors to oral diseases.

The following mechanisms (methodology) of action specify the explanations for bacterial kill by chlorine dioxide. The specific mechanism of action of chlorine dioxide on cells has been debated for a number of years. Early research showed that chlorine dioxide's primary effect was the disruption of protein synthesis, leading to cell death (Benarde et al., 1967). Results from Benarde's studies clearly showed an abrupt inhibition on protein synthesis. Explanations of this occurrence on the cells included possible inhibition of amino acid activation, inactivation of messenger RNA (which prevents translation), and destruction of ribosomes by chlorine dioxide (which causes a loss in cell contents by leakage).

A later study, however, indicated that this might not be the case. Roller et al. studied the effects of chlorine dioxide on dehydrogenase enzymes, protein synthesis, and deoxyribonucleic acid of bacteria (Roller et al., 1986). Results showed that total dehydrogenase enzymes were inhibited completely within the first 5 seconds of reaction by chlorine dioxide and protein synthesis was partially inhibited. The dosage of chlorine dioxide used was found to be proportional to the extent of inhibition. These studies concluded that the primary effect of chlorine dioxide on cells was occurring in an area in the cell other than the dehydrogenase enzymes, protein synthesizing complex, or DNA. It was determined that inhibition of protein synthesis of cells, indeed, contributed to cell death. However, Roller et al. concluded that an impairment of the cell's functions is occurring even before protein synthesis. Chlorine dioxide was shown to not cause cell inactivation by altering or impairing the cell's DNA. An explanation or theory of the cell deaths by chlorine dioxide in this study is by a reaction with or oxidation of components related to enzyme activity of the cell (Roller et al., 1986).

A more recent study on the mechanism of action of chlorine dioxide was done by Berg et al. (1986). Berg et al. studied the effect of chlorine dioxide on membrane functions of *Escherichia coli* and found that the permeability control was impaired, leading to cell death. It was also shown that the inactivation by the chlorine dioxide does not cause a significant loss of intracellular macromolecules existing inside the cell to the surroundings. However, the membrane damage led to the loss of intracellular potassium destroying the transmembrane ionic gradient, which is understood to result in lethal inhibition of the metabolic processes and cell death. Thus, the permeability barrier of the cell was determined to be important to the sensitivity to chlorine dioxide and growth characteristics of the cell (Berg et al., 1986).

The research evidence resulting in the present invention suggests stabilized chlorine dioxide causes bactericidal and bacteriostatic effects on the bacterial cells, which ultimately lead to cell death. These effects can lead to control over the formation of bacterial biofilm and malodorous volatile sulfur compounds, main contributors to oral diseases.

EXAMPLES

Bactericidal activity of stabilized chlorine dioxide oral rinse against polymicrobial biofilm was evaluated (Drake, 2008 and Villhauer et al., 2009).

Materials & Supplies:
*Porphyromonas gingivalis* (Pg broth, BPB+mupirocin agar)
*Peptostreptococcus micros* (Pm broth, MSCN agar)
*Fusobacterium nucleatum* (Schaedler's Broth, CVE agar)
*Actinomyces viscosus* (BHI broth, Cfat+mupirocin agar)
*Streptococcus sanguinis* (TSBYE broth, MSss agar)
ETSBYE broth medium
Neutralizing Broth
Sterile distilled water
0.5% stabilized chlorine dioxide oral rinse
Artificial Saliva+Tryptone+Yeast Extract
Sterile Erlenmeyer Flasks
Pipets (1 ml, 10 ml, 25 ml)
Sterile inoculating loops
100 µl pipet and pipet tips
1000 µl pipet and pipet tips
Dilution plate
Sterile test tubes
12-well Transwell® Permeable Membrane Plate (Corning, Inc.)
Spiral Plate (Spiral Biotech Autoplate Model 4000)

Two 50 ml cultures of each organism were inoculated and incubated according to species requirements: *P. gingivalis* in Pg broth and BPB with mupirocin agar; *P. micros* in Pm broth and MSCN agar; *F. nucleatum* in Schaedler's broth and CVE agar; *A. viscosus* in BHI broth and Cfat with mupirocin agar; *S. sanguinis* in TSBYE broth and MSss agar). The *A. viscosus* and *S. sanguinis* cultures were incubated for 24 hours and the *P. gingivalis*, *P. micros*, and *F. nucleatum* were incubated for 48 hours. After incubation, a gram stain was performed to confirm culture purity and species identification. At 24 hours, the *A. viscosus* and *S. sanguinis* cultures were centrifuged and resuspended in ETSBYE (enriched tryptic soy broth supplemented with yeast extract). A mixed bacterial suspension of *A. viscosus* and *S. sanguinis* was made using the resuspended cultures, which was then inoculated in a 12-well Transwell permeable membrane plate and incubated anaerobically at 37° overnight. The following day, the cultures for the remaining three bacterial species (*P. gingivalis*, *F. nucleatum*, and *P. micros*) were centrifuged and resuspended in ETSBYE. Then a mixed suspension of these three bacterial species was made using the resuspended cultures. The 12-well Transwell plate was removed from the anaerobic chamber and the day old inoculum was removed. Each well was re-inoculated with the new mixed bacterial (*P. gingivalis, F. nucleatum*, and *P. micros*) suspension. The 12-well Transwell plate was then incubated anaerobically for 5 days to produce the polymicrobial biofilm with five bacteria. The plate was re-inoculated with fresh *F. nucleatum* at 48 hours. Fresh ETSBYE was also added at 96 hours to prevent the plate from drying.

After incubation, the plate was removed from the anaerobic chamber and each well was rinsed twice with sterile distilled water ($dH_2O$) to remove unattached cells. Following this rinse, each well was exposed to 0.5% stabilized chlorine dioxide oral rinse (test) or $dH_2O$ (negative control) for 1 minute. Following exposure, each well was rinsed twice with $dH_2O$ to remove any residual rinse and then Artificial Saliva+Tryptone+Yeast Extract (AS+T+Y) was added to each well to sustain the cells until the next exposure. Six hours after the first exposure, a second exposure was performed. For this exposure, the AS+T+Y was removed and each well was exposed to the rinse 0.5% stabilized chlorine dioxide oral rinse or $dH_2O$. Following exposure, the wells were rinsed twice with $dH_2O$, and AS+T+Y was again added to each well to sustain the cells until the following exposure. The plate was placed in the anaerobic chamber overnight. The following day, approximately 18 hours later, a third and final exposure was performed. Before exposure, each well was rinsed once with $dH_2O$ to remove unattached cells and then each well was exposed to stabilized chlorine dioxide oral rinse or $dH_2O$ for 1 minute. After removing the rinse, 1 ml of neutralizing broth was added to each well and the biofilms were scraped using sterile inoculating loops. The biofilms were then harvested (anaerobically incubated at 37°) and processed for spiral plating. The harvested biofilms were diluted and spiral plated onto selective media plates in order to determine the number of each type of bacteria remaining.

Figure 2:
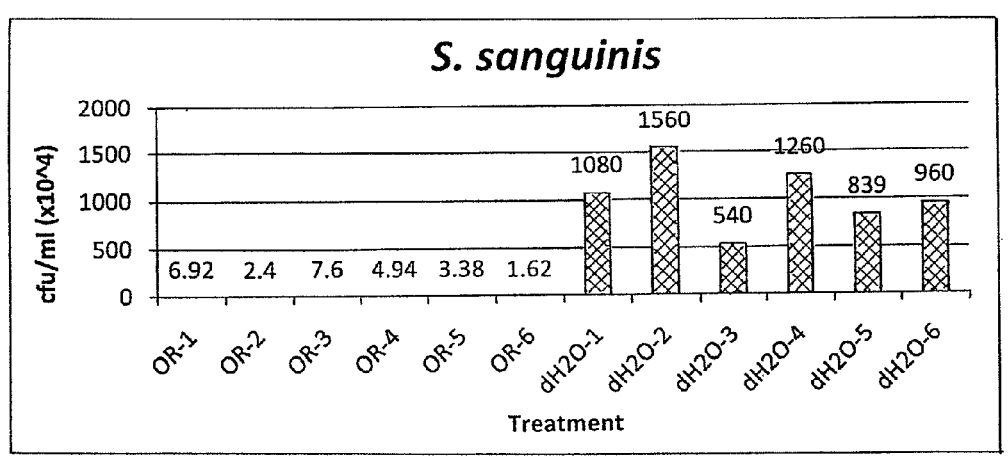
FIG. 2 illustrates the bacterial concentration of biofilm bacteria, *S. sanguinis*, following multiple exposures to 0.5% stabilized chlorine dioxide rinse.
Figure 3:
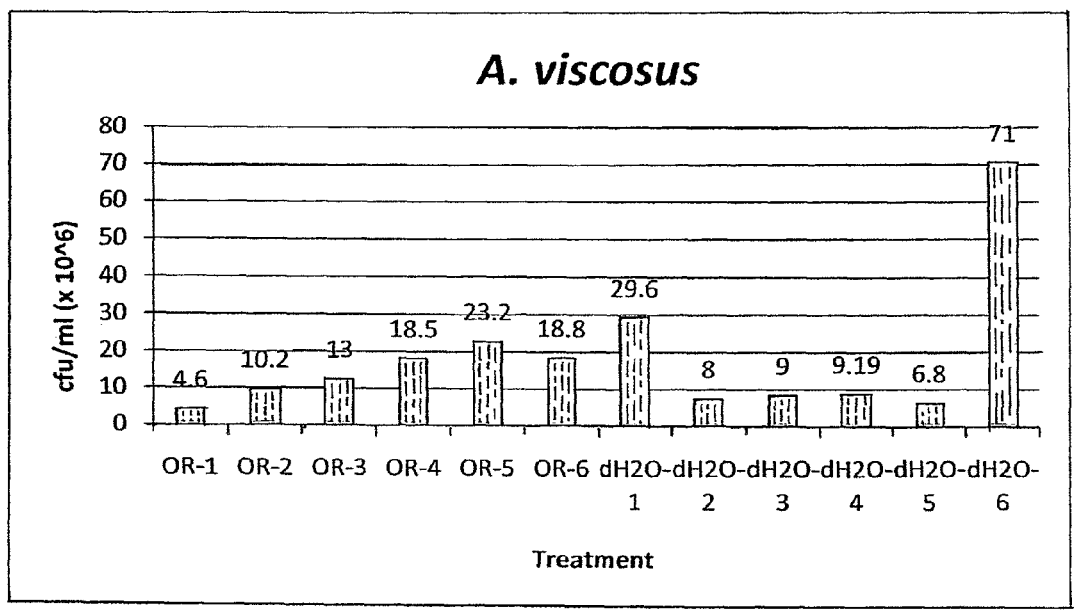
FIG. 3 illustrates the bacterial concentration of biofilm bacteria, *A. viscosus*, following multiple exposures to 0.5% stabilized chlorine dioxide rinse.
Figure 4:
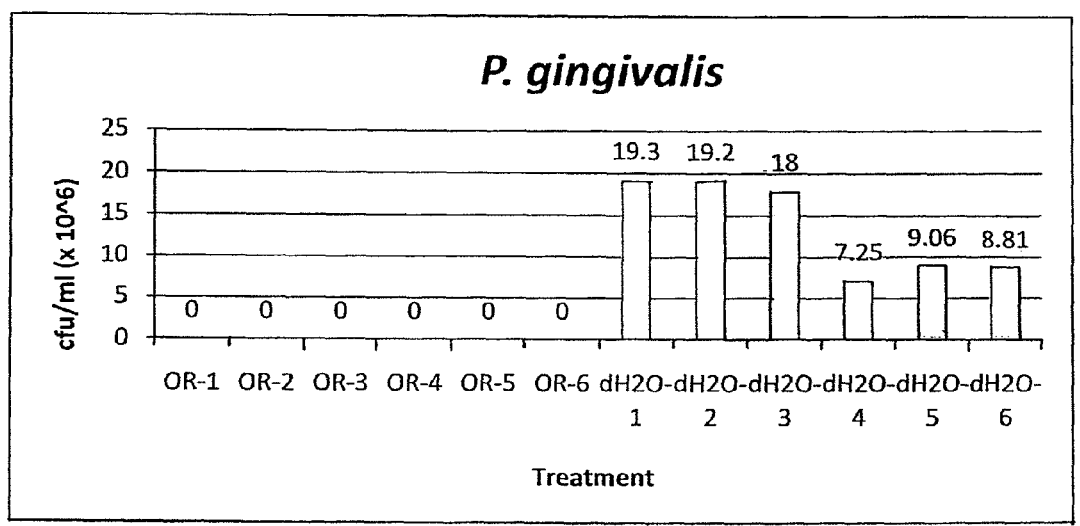
FIG. 4 illustrates the bacterial concentration of biofilm bacteria, *P. gingivalis*, following multiple exposures to 0.5% stabilized chlorine dioxide rinse.
Figure 5:
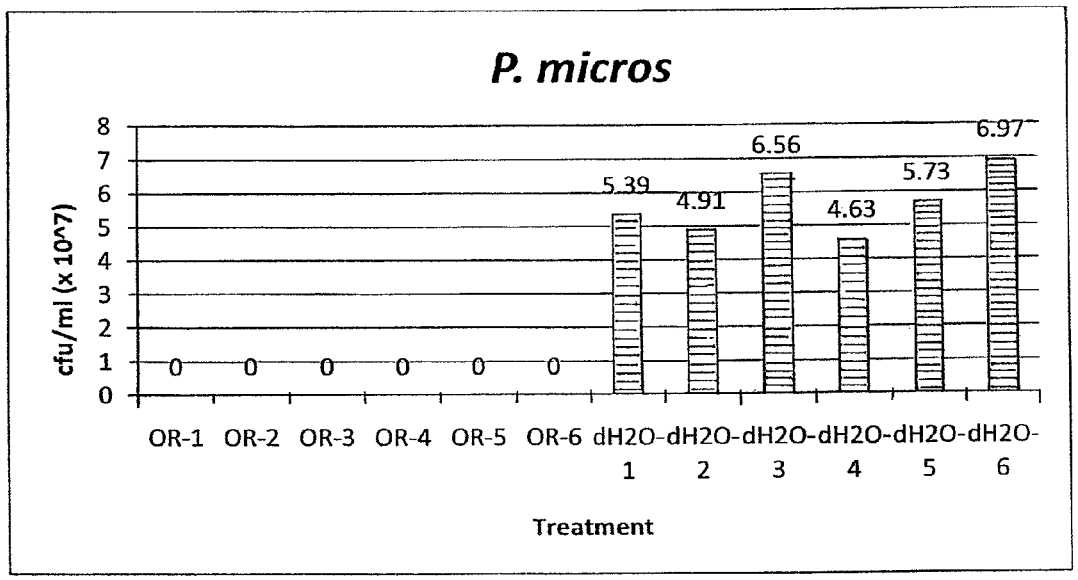
FIG. 5 illustrates the bacterial concentration of biofilm bacteria, *P. micros*, following multiple exposures to 0.5% stabilized chlorine dioxide rinse.
Figure 6:
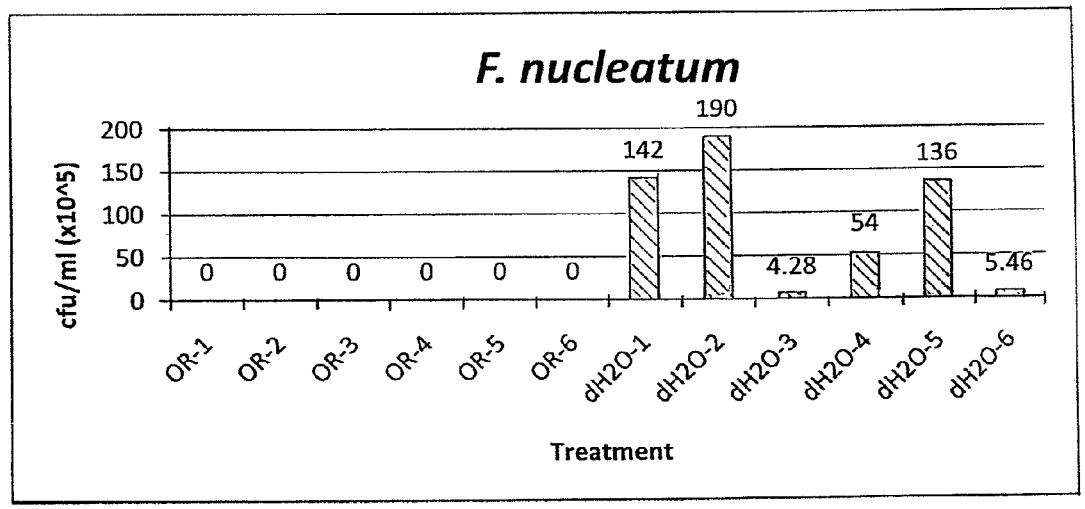
FIG. 6 illustrates the bacterial concentration of biofilm bacteria, *F. nucleatum*, following multiple exposures to 0.5% stabilized chlorine dioxide rinse.

Results of 0.5% stabilized chlorine dioxide oral rinse exposures to the polymicrobial biofilm are shown in Table 1. Table 2 shows the negative control, $dH_2O$, results. FIG. 1 shows the effect of multiples exposures of 0.5% stabilized chlorine dioxide rinse and control ($dH_2O$) on the polymicrobial biofilm. The results found statistically significant reductions of several periodontal pathogens in a polymicrobial biofilm with multiple exposures to 0.5% stabilized chlorine dioxide oral rinse. It was also observed that the regimen resulted in the complete elimination of three periodontal pathogens, *P. gingivalis, P. micros*, and *F. nucleatum* (FIGS. 4-6). There was a reduction of *S. sanguinis*, however was not completely eliminated (FIG. 2). *A. viscosus* was not affected by the oral rinse (FIG. 3). Both *S. sanguinis* and *A. viscosus* are associated with healthy subgingival flora.

the oral cavity comprising a solution of stabilized chlorine dioxide having the concentration in the range of about 0.005% to about 0.800% (w/v) in the form of a one phase rinse and a mixture of acetate, citrate and peroxy buffers to provide a pH in the range of about 6.0 to about 7.4 at the time of composing.

4. A composition as set forth in claim 3 wherein said composition is selected from the groups consisting of a wash, rinse, soak, paste, gel and aerosol spray.

5. A composition as set forth in claim 3 wherein the concentration of the stabilized chlorine dioxide is equal to or greater than 0.5% (w/v).

6. A composition for destroying gram-negative anaerobic, aerobic, and facultative bacteria and gram-positive anaerobic, aerobic, and facultative bacteria resident in a polymicrobial biofilm environment of multiple species of bacteria in the oral cavity comprising a single phase solution of stabilized chlorine dioxide having a concentration in the range of 0.005% to 0.800% (w/v) and a mixture of acetate, citrate and peroxy buffering compounds to provide a pH in the range of 6.0 to 7.4 at the time of composing.

7. A composition as set forth in claim 6 wherein said composition is in a form selected from the group consisting of a wash, rinse, soak, paste, gel and aerosol spray.

TABLE 1

0.5% stabilized chlorine dioxide oral rinse exposure to polymicrobial biofilm.

| | | Stabilize Chlorine Dioxide Treament Trials | | | | | | |
|---|---|---|---|---|---|---|---|---|
| | | OR-1 | OR-2 | OR-3 | OR-4 | OR-5 | OR-6 | |
| Bacteria in biofilm | S. sanguinis | 6.92 | 2.4 | 7.6 | 4.94 | 3.38 | 1.62 | CFUs/ml (×10^4) |
| | A. viscosus | 460 | 1020 | 1300 | 1850 | 2320 | 1880 | |
| | P. gingivalis | 0 | 0 | 0 | 0 | 0 | 0 | |
| | P. micros | 0 | 0 | 0 | 0 | 0 | 0 | |
| | F. nucleatum | 0 | 0 | 0 | 0 | 0 | 0 | |

TABLE 2

Negative control distilled water ($dH_2O$) exposure to polymicrobial biofilm.

| | | Negative Control Treament Trials | | | | | | |
|---|---|---|---|---|---|---|---|---|
| | | $dH_2O$-1 | $dH_2O$-2 | $dH_2O$-3 | $dH_2O$-4 | $dH_2O$-5 | $dH_2O$-6 | |
| Bacteria in biofilm | S. sanguinis | 1080 | 1560 | 540 | 1260 | 839 | 960 | CFUs/ml (×10^4) |
| | A. viscosus | 2960 | 800 | 900 | 919 | 680 | 7100 | |
| | P. gingivalis | 1930 | 1920 | 1800 | 725 | 906 | 881 | |
| | P. micros | 5390 | 4910 | 6560 | 4630 | 5730 | 6970 | |
| | F. nucleatum | 1420 | 1900 | 43 | 540 | 1360 | 55 | |

We claim:

1. A composition for compromising the biofilm attendant in the oral cavity comprising a single phase solution of approximately 0.5% (w/v) concentration of stabilized chlorine dioxide and a mixture of acetate, citrate and peroxy buffering compounds to provide a pH in the range of about 6.0 to about 7.4 at the time of composing for a topical application in the oral cavity.

2. A composition as set forth in claim 1 wherein said composition is an effective bactericide of the following bacteria present in the biofilm: *Porphyromonas gingivalis, Fusobacterium nucleatum*, and *Micromonas micros*.

3. A composition for controlling the formation of bacterial biofilm and the generation of volatile sulphur compounds in 8. A composition as set forth in claim 6 wherein the concentration of stabilized chlorine dioxide is equal to or greater than 0.5% (w/v).

9. A composition expressly intended for penetrating polymicrobial oral biofilms, said composition comprising:

(a) a solution of approximately 0.5% (w/v) concentration of stabilized chlorine dioxide;

(b) a combination of acetate, citrate and peroxy buffering compounds to provide a pH in the range of about 6.0 to about 7.4 at the time of composing;

(c) said composition being single phase and requiring no additional chemical activation other than the chemical properties of the oral cavity and human saliva; and (d) said composition intended to activate within 30 to 60 seconds of being introduced into the oral cavity.

10. A composition as set forth in claim 9 wherein said composition becomes an effective bactericide on gram-negative anaerobic bacteria resident within the biofilm, including *P. gingivaiis, F. nucleatum*, and *M. micros*.

11. A composition as set forth in claim 10 wherein said composition being adapted not to harm certain gram-positive bacteria, including *A. viscosus* and *S. sanguinis*.

* * * * *